United States Patent [19]

Klodowski et al.

[11] Patent Number: 5,174,964
[45] Date of Patent: Dec. 29, 1992

[54] GAS TESTING APPARATUS

[75] Inventors: Harry F. Klodowski, Syracuse; Kenneth B. Barrett, Jamesville; Phil Hider, Marcellus, all of N.Y.

[73] Assignee: Carrier Corporation, Syracuse, N.Y.

[21] Appl. No.: 724,249

[22] Filed: Jul. 1, 1991

[51] Int. Cl.[5] .............................. G01N 30/96
[52] U.S. Cl. ........................ 422/88; 422/58; 422/86; 422/104; 436/167; 116/264; 116/266; 116/273
[58] Field of Search ............ 422/58, 86, 88, 104; 436/167; 116/264, 266, 273

[56] References Cited

U.S. PATENT DOCUMENTS

| | | | |
|---|---|---|---|
| 3,817,707 | 6/1974 | Cummings | 422/104 |
| 4,159,304 | 6/1979 | Shono | 422/104 |
| 4,389,372 | 6/1983 | Lalin | 422/88 |
| 4,459,266 | 7/1984 | Lamoreaux | 422/86 |
| 4,923,806 | 5/1990 | Klodowski | 436/39 |
| 4,986,128 | 1/1991 | Burns | 116/272 X |

OTHER PUBLICATIONS

Brochure "Don't Take Another Oil Sample", Publ. #576-653 ©1988 Carrier Corporation.

Primary Examiner—James C. Housel
Assistant Examiner—Maureen M. Wallenhorst

[57] ABSTRACT

A gas testing apparatus of the type that directs a stream of gas to be tested through a tube containing reagent chemicals. The apparatus has a connector fitting to enable it to be connected to a closed system containing the gas to be tested, a base member having an orifice that reduces the pressure of the gas delivered to the testing tube to near atmospheric, a sliding cover that encloses the testing tube when it is positioned in the holder, and a rising stem indicator that indicates that gas flow has commenced through the tube. The apparatus also has tube seat seals for insuring that all gas entering the apparatus must flow through and not bypass the testing tube.

9 Claims, 2 Drawing Sheets

GAS TESTING APPARATUS

BACKGROUND OF THE INVENTION

This invention relates generally to gas testing devices. More particularly, the invention relates to an apparatus for testing a gas drawn from a closed system for the presence of contaminants by passing the gas through a testing tube mounted in the apparatus.

U.S. Pat. No. 4,923,806 (Klodowski, issued May 9, 1990) describes an apparatus for testing refrigerant drawn from a closed system for the presence of contaminants. Briefly summarized, the '806 patent describes a testing apparatus in which a very small flow of refrigerant from a closed system such as an air conditioning or refrigeration system is removed from the system, reduced in pressure to near atmospheric and directed through a testing tube. The testing tube contains reagent chemicals that produce a visual indication of the presence of contaminants in the refrigerant. The testing apparatus has means for connecting the apparatus to the system to be tested, pressure reducing means, means for receiving the inlet end of the tube and sealing means for providing a fluid tight fit between the receiver means and the exterior of the tester tube, a testing tube holder having openings at each end and a central cavity into which a testing tube can be inserted. The testing tube has tapered and sealed ends to isolate the chemicals during shipping and storage.

To conduct a test, the ends of the glass testing tube are broken off, thus establishing an open gas flow path through the tube. The now open ended testing tube is inserted into the apparatus so that its inlet end is seated in the receiver means and sealed by the sealing means. The testing apparatus is then connected to the refrigeration system to be tested and a flow of refrigerant flow established through the apparatus and the installed testing tube. After a predetermined time, the flow is stopped and a visual inspection is made of the condition of the reagent chemicals to determine the presence, if any, of contaminants in the system.

The commercialized embodiment of the testing apparatus described in the '806 patent has proven quite successful. Experience with that embodiment, however, has suggested improvements to the apparatus. The current commercial embodiment does not include any flow indicating means. The extremely small refrigerant flow is audible but, in environments having moderate to high background noise, it is difficult or impossible to hear the sound of the flow. Liquid refrigerant can sometimes form at the exit of the testing tube and drip on to the interior wall of the apparatus, where it evaporates. The thermal stress caused by the evaporating refrigerant has sometimes caused the plastic material of the testing tube holder to crack.

SUMMARY OF THE INVENTION

The present invention is a gas testing apparatus that offers improved ease of use and additional capability over the proven and commercially successful prior art apparatus. The apparatus accepts the testing tubes presently in use.

The gas testing apparatus of the present invention is more convenient to use than the prior art apparatus and includes a flow indicator at its outlet opening. The apparatus has a base member and a sliding cover that cannot be separated from the base member in normal use. The flow indicator provides a positive indication of refrigerant flow through the apparatus. The indicator has an inlet seat into which the outlet end of the testing tube fits when the tube is inserted into the testing tube holder, making a fluid tight seal. The refrigerant thus cannot bypass the flow indicator and is constrained to flow through it, preventing any liquid refrigerant formed from dripping on to the inner wall of the testing apparatus. A spring engages the flow indicator to urge the indicator in the direction of the inlet end of the testing tube holder, assuring a close fit between both the inlet end of the testing tube and the receiving means and the outlet end of the testing tube and the flow indicator.

BRIEF DESCRIPTION OF THE DRAWINGS

The accompanying drawings form a part of the specification. Throughout the drawings, like reference numbers identify like elements.

DESCRIPTION OF THE PREFERRED EMBODIMENT

Figures 1, 5:
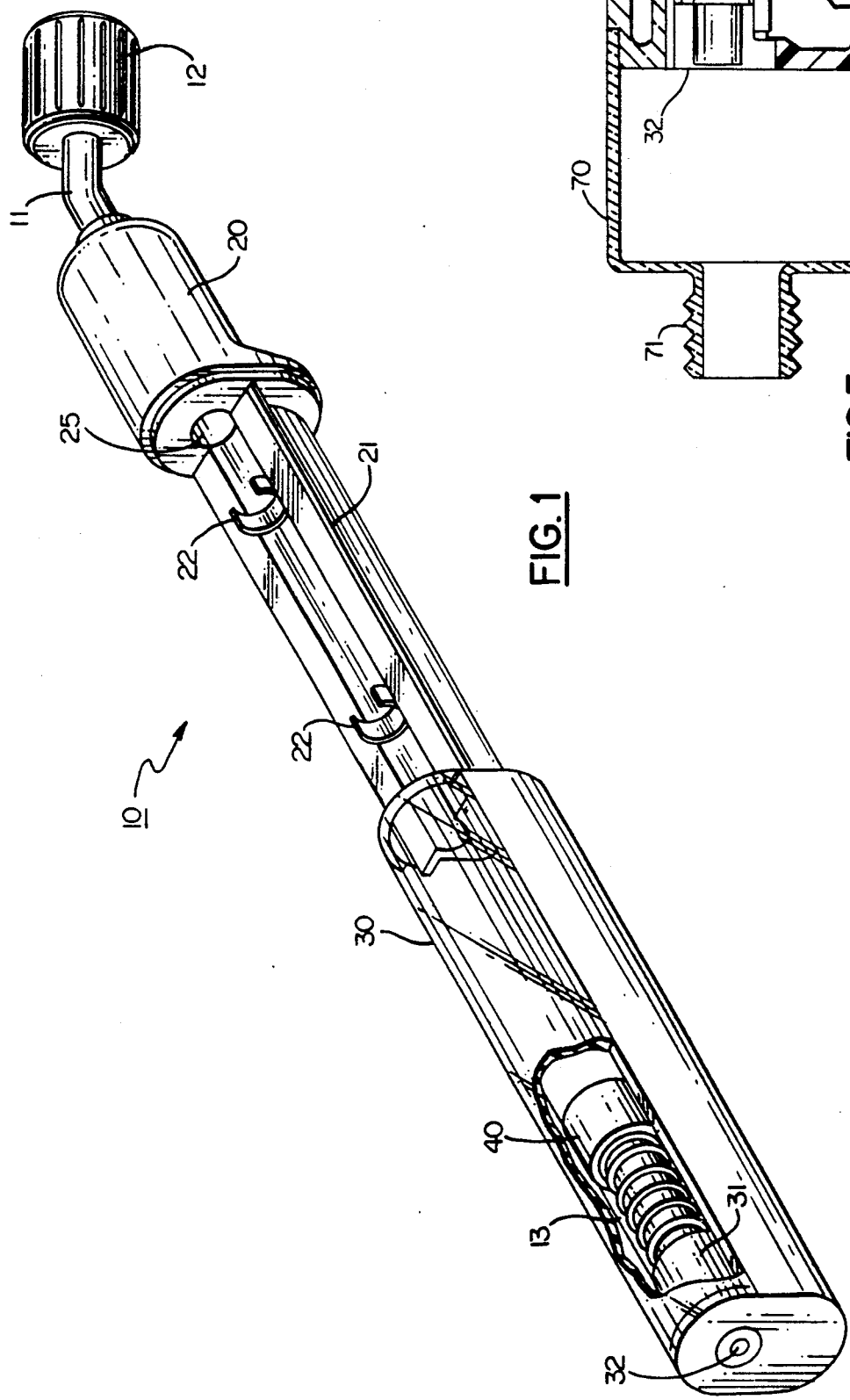
FIG. 1 is a partially sectioned perspective view of a gas testing apparatus of the present invention in its open or LOAD position.
FIG. 5 is a sectioned elevation view of a portion of the apparatus of the present invention in an alternate embodiment.

FIG. 1 illustrates a gas testing apparatus adapted for use in testing a gas such as the refrigerant in an air conditioning or refrigeration system for the presence of entrained contaminants. FIG. 1 shows gas testing apparatus 10 in its Open or LOAD position. Apparatus 10 comprises base member 20 having track 21. Sliding cover 30 attaches to base member 20 and slides on track 21. Tube 11 connects base member 20 to connector fitting 12. Connector fitting 12 is the female counterpart to the male Schrader ® fitting almost universally found in air conditioning and refrigeration systems for charging refrigerant. Slideably mounted in cover 30 is flow indicator 40. Spring 13 urges flow indicator 40 away from cover shoulder 31. There is an opening 32 in one end of cover 30, the function of which will be described below. Testing tube supports 22 are fitted to base member 20.

Figure 2:
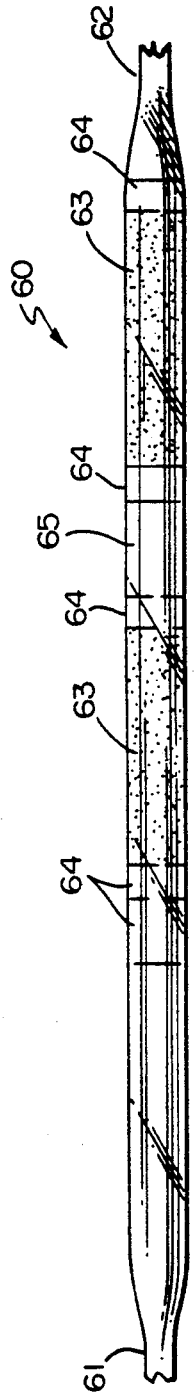
FIG. 2 is a side elevation view of a gas testing tube used with the apparatus of the present invention.

FIG. 2 depicts a refrigerant testing tube of the type intended for use with gas testing apparatus 10. Testing tube 60 is made of glass and has inlet end 61 and outlet end 62. Within testing tube 60 are beds of reagent chemicals 63, suitable for the tests to be performed on the refrigerant, separated by appropriate screens 64 and filters 65. During manufacture of testing tube 60, inlet and outlet ends 61 and 62 are heated and drawn to form a seal, isolating the reagent chemicals from the atmosphere outside the tube. In preparation for conducting a test, the sealed ends are broken off testing tube 60 so that a gas flow path exists from inlet end 61 to outlet end 62, enabling a refrigerant to flow through the tube and contact the reagent chemical beds.

Figure 3:
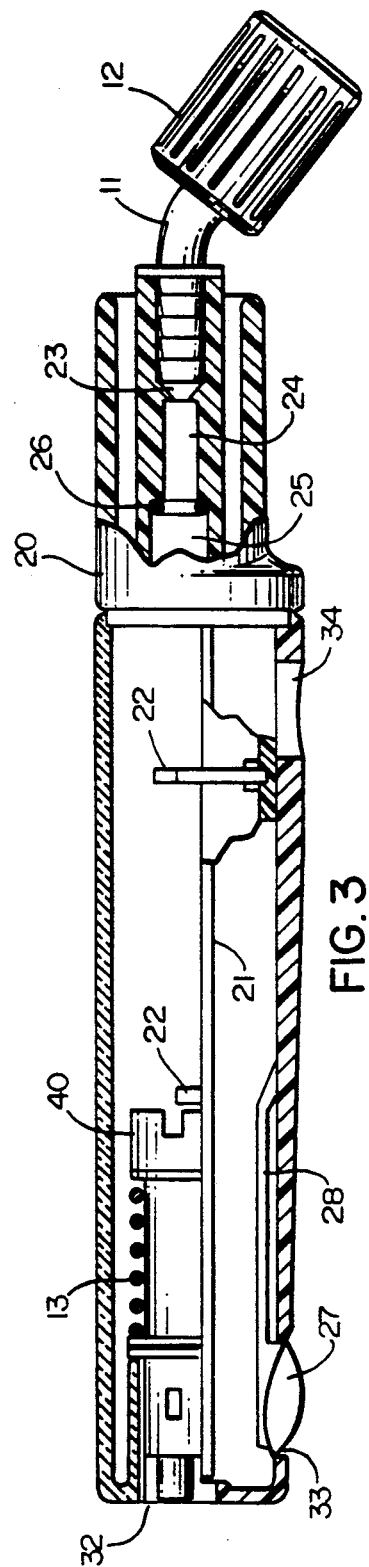
FIG. 3 is a partially sectioned elevation view of a gas testing apparatus of the present invention in its shut or TEST/STORE position.

FIG. 3 illustrates gas testing apparatus 10 in its shut or STORE/TEST position and enables a view of features of apparatus 10 not visible in FIG. 1. Sliding cover 30 may be latched in either its STORE/TEST position by means of latch button 27 and detent 33 or in its LOAD position by means of button 27 and detent 34. Button 27 is urged into either detent when cover 30 is suitably aligned with base member 20 by suitable urging means acting upon arm 28. Passage 24 connects orifice 23 with tube receiver 25. Seal 26, preferably an O-ring, prevents leakage of gas when a testing tube is inserted into receiver 25.

Figure 4:
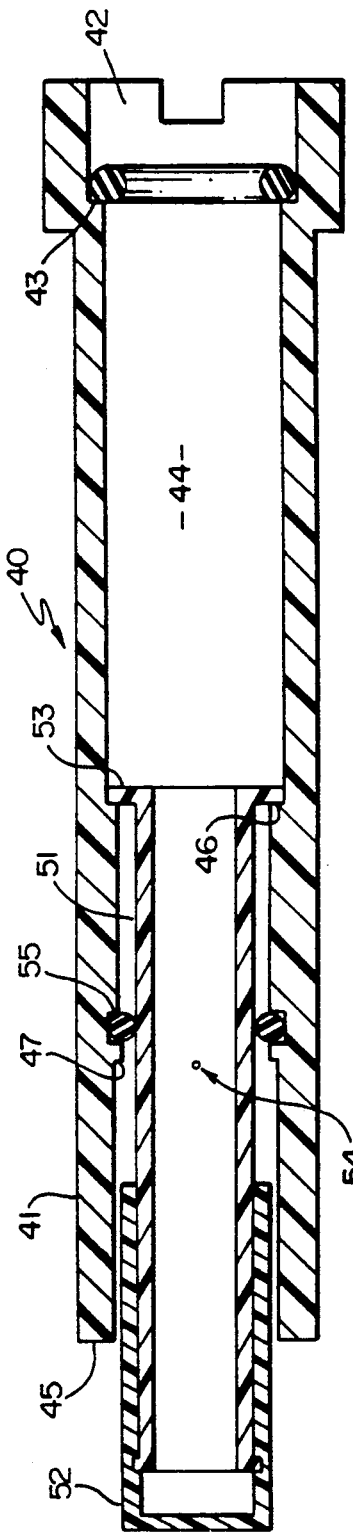
FIG. 4 is a sectioned elevation view of the flow indicator of the apparatus of the present invention.

FIG. 4 depicts flow indicator 40 in more detail. Slideably mounted in sleeve 41 of indicator 40 is stem 51. Sleeve 41 has tube receiver 42 and outlet end 45. At one end of stem 51 is fitted end cap 52. The other end of stem 51 is open and has flange 53. With end cap 52 fitted to stem 51, the only outlet for gas entering stem 51 through the shoulder end is bleed port 54. Seal 55, preferably an O-ring, prevents leakage of gas through the annular space between the exterior of stem 51 and the interior of sleeve 41. Similarly, seal 43, also preferably an O-ring, prevents leakage of gas out of flow indicator 40 when a testing tube is inserted into chamber 44. Sleeve shoulders 46 and 47, respectively interacting with flange 53 and end cap 52, define the limits of relative motion between stem 51 and sleeve 41.

To prepare gas testing apparatus 10 for a test, sliding cover 30 is first placed and latched in its LOAD position. Testing tube 60 is readied by breaking off the end tips and leaving inlet end 61 and outlet end 62 open. The tube is placed in base member 20 so that it rests in tube supports 22 and inlet end 61 extends into tube receiver 25 and contacts seal 26. Sliding cover 30 is then moved to and latched in its STORE/TEST position. As cover 30 moves into the STORE/TEST position, outlet end 62 of testing tube 60 enters tube receiver 42 of flow indicator 40, contacting seal 43 and extending into chamber 44. Spring 13 urges flow director 40 against testing tube 60, insuring a good seat between the tube and seal 43 and also between the tube and seal 26 at the inlet end of the tube. End cap 52 is in contact with sleeve shoulder 47 and does not protrude out of end passage 32 in cover 30. All or that portion of sliding cover 30 that is over tube supports 22 when cover 30 is in its STORE/TEST position is preferably made of a transparent material such as a transparent plastic so that the presence or absence of a testing tube in apparatus 10 can be determined without opening cover 30.

To commence a test, connector fitting 12 is attached to a suitable fitting on a refrigeration or air conditioning system to be tested. Refrigerant then flows through the connector fitting, tube 11 and orifice 23, where the refrigerant pressure is reduced to near atmospheric. The refrigerant passes into passage 24 and enters testing tube 60 through open inlet end 61. The refrigerant flows through testing tube 60, passing over the reagent chemicals, and exits the tube through outlet end 62 to enter chamber 44 of flow indicator 40. Initially, pressure will build up in chamber 44 and the interior of stem 51, causing stem 51 to move until flange 53 contacts sleeve shoulder 46. A further increase of pressure is prevented as the refrigerant will then vent out of bleed port 54. When flange 53 is in contact with sleeve shoulder 46, end cap 52 protrudes out of passage 32 giving a visual indication that there has been a pressure buildup in gas testing apparatus 10 and that therefore there is flow in testing tube 60. End cap 52 is preferably made of a high visibility color to facilitate its observation.

After a time and in a manner prescribed by the type of testing tube and procedure being employed, flow through the tube is stopped by disconnecting connector fitting 12 from the system and the test results are determined.

Because of the construction of base member 20 and flow indicator 40, particularly seals 43 and 55, all refrigerant entering testing apparatus 10 must pass through testing tube 60 and exit the apparatus through bleed port 54, with no possibility that liquid refrigerant may collect and drip on to base member 20 or cover 30.

In some cases, it may be desirable to collect the refrigerant that exits testing apparatus 10 through bleed port 54. FIG. 5 shows a portion of an alternate embodiment of the present invention that enables collection of refrigerant. FIG. 5 shows the end of testing apparatus 10 in which is mounted flow indicator 40. Affixed to and enclosing that end is refrigerant receiver 70 having threaded outlet 71. Refrigerant receiver 70 is sized so that it will not interfere with the movement of end cap 52 as it extends out of passage 32 to indicate refrigerant flow. Refrigerant receiver 70 is preferably made of a transparent material so that a user may observe the position of flow indicator 40 through the receiver wall. Threaded outlet 71 allows auxiliary, such as refrigerant collection and storage, devices (not shown) to be connected to testing apparatus 10.

What is claimed is:

1. A gas testing apparatus for use with a gas testing tube and in which a gas to be tested flows in an upstream to downstream direction through said apparatus comprising:
   a connector fitting adapted to connect to a source of gas to be tested;
   a base member having
      a pressure reducing orifice,
      a first testing tube receiver and
      a fluid flow conduit for directing a flow of gas to be tested from said connector fitting through said pressure reducing orifice to said first testing tube receiver;
   a cover slideably mounted to said base member, said cover having
      a LOAD position in which said cover is open and
      a TEST/STORE position in which said cover is shut;
   means mounted to said base member for latching said cover in both said open or LOAD position and in said shut or TEST/STORE position; and
   a flow indicator mounted in said cover, said flow indicator having
      a second testing tube receiver and
      means for indicating that there is a flow of gas through said testing tube.

2. The gas testing apparatus of claim 1 in which said latching means comprises:
   a LOAD position detent and a TEST/STORE position detent in said cover;
   a latch button on an arm mounted on said base member in a position so that said button may extend into said detents; and
   means for urging said latch button into said detents.

3. The gas testing apparatus of claim 1 in which said flow indicating means comprises a rising stem that protrudes from said cover when gas flow is established through said testing tube.

4. The gas testing apparatus of claim 3 in which said rising stem protrudes longitudinally from said cover.

5. The gas testing apparatus of claim 3 in which said rising stem has a closed end, an open end, a bleed port and an outer wall and is slideably mounted in a sleeve of said flow indicator, said sleeve, having an inner wall, said flow indicator includes means for preventing fluid flow between said rising stem outer wall and said sleeve inner wall, and said second testing tube receiver is in upstream fluid flow relationship with said rising stem open end through said sleeve.

6. The gas testing apparatus of claim 5 in which said fluid flow preventing means is an O-ring.

7. The gas testing apparatus of claim 1 in which said gas testing tube has an outer wall and said first testing tube receiver and said second testing tube receiver have inner walls, and said first testing tube receiver and said second testing tube receiver include means for preventing fluid flow between said gas testing tube outer wall and said first testing tube receiver and said second testing tube receiver inner walls.

8. The gas testing apparatus of claim 1 further comprising a refrigerant receiver, having means for removeably affixing auxiliary devices, extending from an end of said cover.

9. The gas testing apparatus of claim 8 in which said means for removeably affixing auxiliary devices comprises a threaded outlet from said refrigerant receiver.

* * * * *